US011315248B2

(12) United States Patent
Sughrue et al.

(10) Patent No.: US 11,315,248 B2
(45) Date of Patent: Apr. 26, 2022

(54) IDENTIFYING INVALID MEDICAL IMAGES

(71) Applicant: Omniscient Neurotechnology Pty Limited, Sydney (AU)

(72) Inventors: Michael Edward Sughrue, Sydney (AU); Stephane Philippe Doyen, Glebe (AU); Peter James Nicholas, South Hurstville (AU); Jacob David Roberts, Encinitas, CA (US)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/337,365

(22) Filed: Jun. 2, 2021

(65) Prior Publication Data

US 2021/0390690 A1   Dec. 16, 2021

Related U.S. Application Data

(60) Provisional application No. 63/037,235, filed on Jun. 10, 2020.

(51) Int. Cl.
*G06T 7/00* (2017.01)
*G16H 30/20* (2018.01)
(Continued)

(52) U.S. Cl.
CPC ........... *G06T 7/0012* (2013.01); *G16H 30/20* (2018.01); *G16H 30/40* (2018.01); *G06T 2207/10088* (2013.01); *G06T 2207/30016* (2013.01)

(58) Field of Classification Search
CPC ......... G06T 7/0012; G06T 2207/10088; G06T 2207/30016; G06T 2207/10081;
(Continued)

(56) References Cited

U.S. PATENT DOCUMENTS

2008/0205587 A1   8/2008   Nakanishi
2016/0120495 A1   5/2016   Miyazawa
(Continued)

FOREIGN PATENT DOCUMENTS

CN    110827291 A   *   2/2020
EP    3467766           4/2019

OTHER PUBLICATIONS

Fan et al. The Human Brainnetome Atlas: A New Brain Atlas Based on Connectional Architecture (Year: 2016).*

(Continued)

*Primary Examiner* — Vu Le
*Assistant Examiner* — Winta Gebreslassie
(74) *Attorney, Agent, or Firm* — Fish & Richardson P.C.

(57) ABSTRACT

Methods, systems, and apparatus, including computer programs encoded on computer storage media, for identifying one or more invalid images characterizing the brain of a patient. One of the methods includes obtaining a data object comprising one or more images characterizing a brain of a patient; processing the data object to determine one or more particular images that are invalid; and providing, for display to a user on a graphical interface, data characterizing i) each particular image and ii) a respective reason that each particular image is invalid selected from a set of possible reasons that an image may be invalid.

21 Claims, 5 Drawing Sheets

(51) Int. Cl.
*G06T 7/11* (2017.01)
*G16H 30/40* (2018.01)

(58) Field of Classification Search
CPC .......... G06T 2207/30004; G06T 2207/10116; G16H 30/20; G16H 30/40
See application file for complete search history.

(56) References Cited

U.S. PATENT DOCUMENTS

2019/0059780 A1    2/2019   Lee et al.
2020/0203002 A1*   6/2020   Amthor .................. G16H 30/40

OTHER PUBLICATIONS

Brainder.org [online], "The NIFTI file format", dated Sep. 23, 2012, retrieved Nov. 16, 2021, retrieved from URL <https://brainder.org/2012/09/23/the-nifti-file-format/>, 37 pages.
dicomstandard.org [online], "About DICOM: Overview," available on or before Jun. 10, 2020, retrieved on Jul. 16, 2021, retrieved from URL <https://www.dicomstandard.org/about-home>, 1 page.
International Search Report and Written Opinion in International Appln. No. PCT/AU2021/050585, dated Sep. 1, 2020, 10 pages.
Power et al., "Spurious but systematic correlations in functional connectivity MRI networks arise from subject motion," NeuroImage, Feb. 2012, 59(3):2142-54.

* cited by examiner

IDENTIFYING INVALID MEDICAL IMAGES

CROSS-REFERENCE TO RELATED APPLICATIONS

This application claims the benefit under 35 U.S.C. § 119(e) of the filing date of U.S. Patent Application No. 63/037,235, for Identifying Invalid Medical Images which was filed on Jun. 10, 2020, and which is incorporated here by reference.

BACKGROUND

This specification relates to processing data related to the brain of a patient, e.g., functional magnetic resonance imaging (MRI) data, diffusion weighted imagery, and/or diffusion tractography data.

Brain functional connectivity data characterizes, for each of one or more pairs of locations within the brain of a patient, the degree to which brain activity in the pair of locations is correlated.

One can gather data related to the brain of the patient by obtaining and processing images of the brain of the patient, e.g., using magnetic resonance imaging (MRI), diffusion tractography (DT) imaging, or functional MRI imaging (fMRI). Diffusion tensor imaging uses magnetic resonance images to measure diffusion of water in a human brain. One can use the measured diffusion to generate images of neural tracts and corresponding white matter fibers of the subject brain.

Data related to the brain of a single patient can be highly complex and high-dimensional, and therefore difficult for a clinician to manually inspect and parse, e.g., to plan a surgery or diagnose the patient for a brain disease or mental disorder.

SUMMARY

This specification relates to a system configured to process images characterizing the brain of a patient in order to determine whether the images are valid. If one or more images are invalid, then the system can display (e.g., to a user of the system) data identifying the invalid images and, optionally, one or more reasons that the images are invalid. In some implementations, the system can automatically process one or more of the invalid images to generate updated images that are valid.

In some implementations, the system processes each brain image using tests that determine the validity of the brain image. In some such implementations, the system processes each brain image using multiple sets of tests that each correspond to a respective different image format. For example, the system can process the brain image, having a first format, using a set of first tests corresponding to the first format. The system can then process each brain image to generate respective reformatted brain images that have a second format, and process each reformatted brain image using a set of second tests corresponding to the second format.

In general, one innovative aspect of the subject matter described in this specification can be embodied in methods that include the actions of: obtaining a data object comprising one or more images characterizing a brain of a patient; processing the data object to determine one or more particular images that are invalid; and providing, for display to a user on a graphical interface, data characterizing i) each particular image and ii) a respective reason that each particular image is invalid selected from a set of possible reasons that an image may be invalid.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. In particular, one embodiment includes all the following features in combination. Processing the data object to determine one or more particular images that are invalid can include, for each image: processing, for each of a plurality of predetermined tests, the image according to the test to generate a respective test output; and determining whether the image is invalid according to the plurality of generated test outputs. The set of possible reasons that an image may be invalid comprises one or more of: a header or data from a file of the image cannot be accessed; a shape of data characterizing the image is inconsistent; the image does not have enough time frames or gradient directions; data characterizing the image is not consistent with standard neuroimaging data; the image does not have correct 3D or 4D dimensionality; metadata of the image is invalid; a file of the image does not match a standard schema; a file of the image cannot be opened using standard tooling; or voxel data characterizing the image does not have valid values. The images characterizing the brain of the patient can include one or more of: one or more MRI images; one or more fMRI images; or one or more diffusion tractography images. Determining that an image is invalid can include one or more of: determining that the image has been corrupted; determining that the image is improperly formatted; or determining that the image does not follow one or more predetermined protocols. Obtaining the data object can include: obtaining, by a local system of a user device of the user, the data object; and uploading the data object from the local system of the user device to a non-local system of a non-local device. Processing the data object can include one or more of: processing the data object using a local system of a user device of the user; or processing the data object using a non-local system of a non-local device. Each image in the data object can have a first format; and processing the data object to determine one or more particular images that are invalid can include: processing, at a first time step, each image according to one or more first tests; processing, for each image, the image to generate a reformatted image having a second format; and processing, at a second time step, each reformatted image according to one or more second tests. The first format can be a DICOM format and the second format can be a NIfTI format. Processing each image at the first time step can include processing each image using a local system of a user device of the user; and processing each reformatted image at the second time step can include processing each reformatted image using a non-local system of a non-local device. The method can further include, in response to determining that one or more images are valid, processing the one or more valid images using an image processing system to generate a clinically relevant output. The clinically relevant output can include connectivity data that characterizes, for each first parcellation and second parcellation of a plurality of parcellations, a correlation between brain activity of the first parcellation and brain activity of the second parcellation in the brain of the patient. The method can further include: generating, for each of one or more of the particular images, a recommendation for updating the particular image to make the particular image valid; and providing, for display to the user on the graphical interface, data characterizing the one or more recommendations.

Another innovative aspect of the subject matter described in this specification can be embodied in a system including one or more computers and one or more storage devices storing instructions that are operable, when executed by the one or more computers, to cause the one or more computers to perform operations including: obtaining a data object comprising one or more images characterizing a brain of a patient; processing the data object to determine one or more particular images that are invalid; and providing, for display to a user on a graphical interface, data characterizing i) each particular image and ii) a respective reason that each particular image is invalid selected from a set of possible reasons that an image may be invalid.

The foregoing and other embodiments can each optionally include one or more of the following features, alone or in combination. In particular, one embodiment includes all the following features in combination. Processing the data object to determine one or more particular images that are invalid can include, for each image: processing, for each of a plurality of predetermined tests, the image according to the test to generate a respective test output; and determining whether the image is invalid according to the plurality of generated test outputs. The set of possible reasons that an image may be invalid can include one or more of: a header or data from a file of the image cannot be accessed; a shape of data characterizing the image is inconsistent; the image does not have enough time frames or gradient directions; data characterizing the image is not consistent with standard neuroimaging data; the image does not have correct 3D or 4D dimensionality; metadata of the image is invalid; a file of the image does not match a standard schema; a file of the image cannot be opened using standard tooling; voxel data characterizing the image does not have valid values; or voxel data characterising the diffusion weighted image is not sufficient for constrained spherical deconvolution (CSD). If this model does not fit within expected bounds, then the data may be corrupt. There can be an additional validation step where a subset of the diffusion weighted image is used to fit a constrained spherical deconvolution (CSD) model. If this model does not fit within expected bounds, then the data may be corrupt. The images characterizing the brain of the patient can include one or more of: one or more MRI images; one or more fMRI images; or one or more diffusion tractography images. Determining that an image is invalid can include one or more of: determining that the image has been corrupted; determining that the image is improperly formatted; or determining that the image does not follow one or more predetermined protocols. Obtaining the data object can include: obtaining, by a local system of a user device of the user, the data object; and uploading the data object from the local system of the user device to a non-local system of a non-local device. Processing the data object can include one or more of: processing the data object using a local system of a user device of the user; or processing the data object using a non-local system of a non-local device.

Particular embodiments of the subject matter described in this specification can be implemented so as to realize one or more of the following advantages.

When uploading brain images to a processing tool or a storage system, users might upload images that have been corrupted, that are improperly protocoled, or that are not the images the user intended to upload. In some cases, the uploading process might be time consuming, and it is not evident to the user that the images are invalid until the end of the time-consuming process. In some other cases, e.g., when the user is uploading the images for storage and later processing, the user might not become aware that the images are invalid until hours, days, or weeks after uploading, at which time it might be difficult or impossible to recover valid images. Using techniques described in this specification, a system can automatically determine that one or more images are invalid before or during the upload process, saving time for the user and resulting in improved outcomes for patients, users and/or clinicians, especially when effective care requires time sensitive investigations.

Furthermore, when an image is invalid, often it is not clear to the user why the image is invalid, and what steps must be taken to correct the issue. Using techniques described in this specification, a system can automatically determine the reason that an image is invalid and present the reason to the user. In some cases, the system can generate suggestions to the user for making an efficient correction to the invalid images. In some implementations, the system can automatically generate an updated valid version of the image, without requiring user input. This can further save time for the user and result in improved health outcomes for patients.

In addition, data related to the brain of a single patient can be highly complex and high-dimensional, and therefore difficult for a clinician to manually inspect and parse, e.g., to plan a surgery or diagnose the patient with a brain disease or mental disorder. For example, a correlation matrix, e.g., a correlation matrix of fMRI data, of the brain of a patient can be segmented into more than a hundred parcellations, e.g., into 379 parcellations. As a result, a single correlation matrix can have more than 10,000 elements, e.g., more than 70,000 elements.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a system that can process images characterizing the brain of a patient, e.g., MRI or diffusion tractography images, to determine whether the images are invalid.

In this specification, a brain image is "invalid" if the brain image fails one or more validity criteria for storing, displaying, and/or processing the brain image. For example, a brain image may be invalid if the image fails one or more validity criteria related to processing the brain image using a machine learning model to generate a clinically-relevant model output for the patient. As a particular example, an invalid brain image may be a brain image that (i) has been corrupted, (ii) is improperly formatted according to a particular formatting standard, and/or (iii) fails to follow one or more protocols, e.g., privacy or safety protocols. In this specification, a model output is "clinically relevant" if the model output represents an answer to a question that a trained clinician might ask in clinical practice treating patients, e.g., a question asked by a clinician in order to treat a patient with a specific disease.

In order to determine whether one or more of the images are invalid, the system can process each image using one or more predetermined tests, where each test corresponds to one or more validity criteria. That is, if a brain image fails a particular test, then the brain image does not meet the criteria corresponding to the particular test, and therefore the brain image is invalid.

Figure 1A:
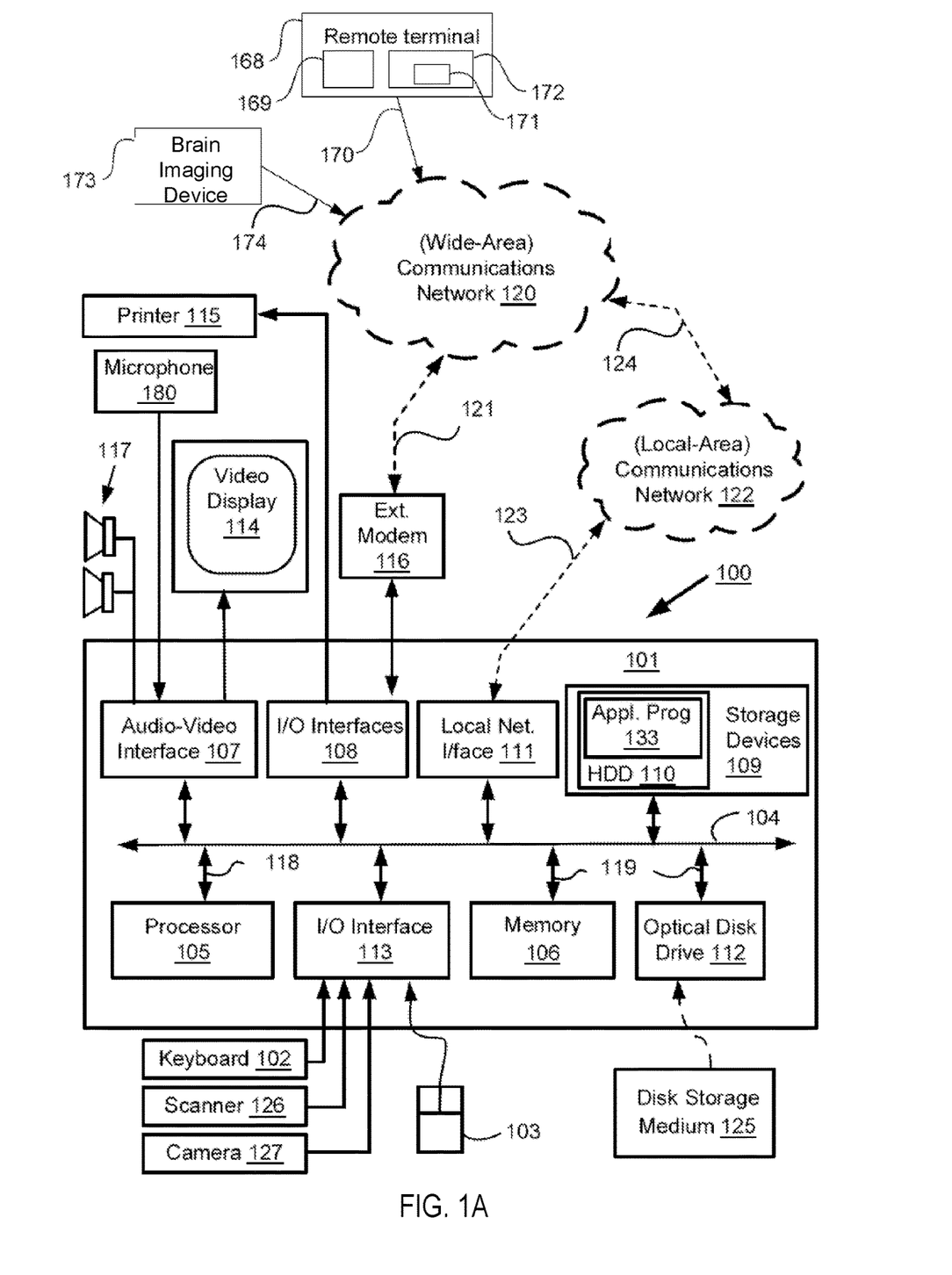
FIG. 1A and FIG. 1B are diagrams that illustrate an example computer system for use in processing medical images.
Figure 1B:
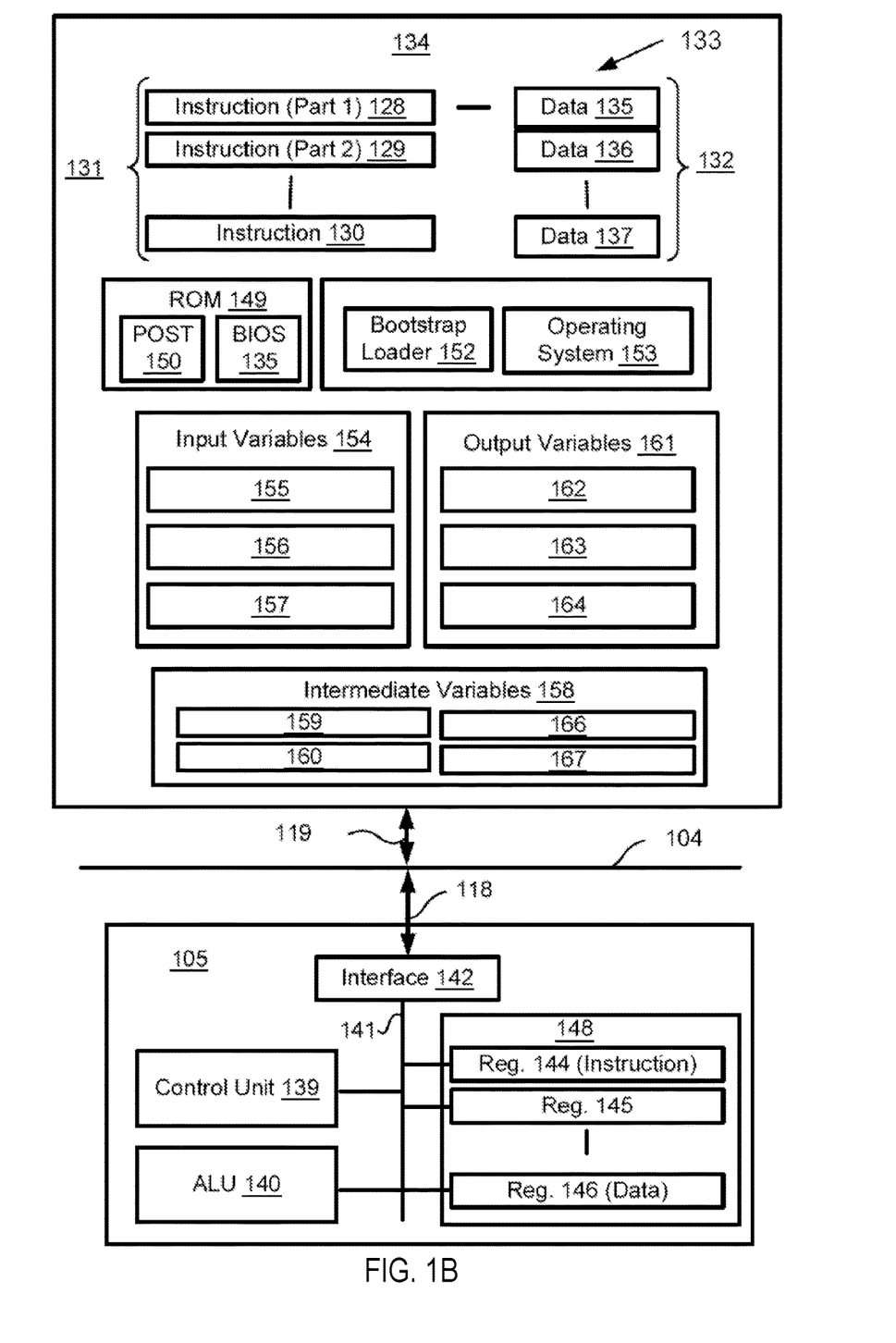

FIGS. 1A and 1B are block diagrams of a general-purpose computer system 100 upon which one can practice arrangements described in this specification. The following description is directed primarily to a computer server module 101. However, the description applies equally or equivalently to one or more remote terminals 168.

As seen in FIG. 1A, the computer system 100 includes: the server computer module 101; input devices such as a keyboard 102, a pointer device 103 (e.g., a mouse), a scanner 126, a camera 127, and a microphone 180; and output devices including a printer 115, a display device 114 and loudspeakers 117. An external Modulator-Demodulator (Modem) transceiver device 116 may be used by the computer server module 101 for communicating to and from the remote terminal 168 over a computer communications network 120 via a connection 121 and a connection 170. The aforementioned communication can take place between the remote terminal 168 and "the cloud" which in the present description comprises at least the one server module 101. The remote terminal 168 typically has input and output devices (not shown) which are similar to those described in regard to the server module 101. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer server module 101 typically includes at least one processor unit 105, and a memory unit 106. For example, the memory unit 106 may have semiconductor random access memory (RAM) and semiconductor read only memory (ROM). The remote terminal 168 typically includes as least one processor 169 and a memory 172. The computer server module 101 also includes a number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may include an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial or parallel connectivity; the former may be implemented according to the Universal Serial Bus (USB) standards and having corresponding USB connectors (not illustrated). Storage memory devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119.

The techniques described in this specification may be implemented using the computer system 100, e.g., may be implemented as one or more software application programs 133 executable within the computer system 100. In some implementations, the one or more software application programs 133 execute on the computer server module 101 (the remote terminal 168 may also perform processing jointly with the computer server module 101), and a browser 171 executes on the processor 169 in the remote terminal, thereby enabling a user of the remote terminal 168 to access the software application programs 133 executing on the server 101 (which is often referred to as "the cloud") using the browser 171. In particular, the techniques described in this specification may be effected by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules performs the described techniques and a second part and the corresponding code modules manage a user interface between the first part and the user.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product.

Software modules for that execute techniques described in this specification may also be distributed using a Web browser.

The software 133 is typically stored in the HDD 110 or the memory 106 (and possibly at least to some extent in the memory 172 of the remote terminal 168). The software is loaded into the computer system 100 from a computer readable medium, and executed by the computer system 100. Thus, for example, the software 133, which can include one or more programs, may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. For example, through manipulation of the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 can execute. The POST program 150 can be stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 can activate the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high-level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source 173, e.g., a brain imaging device 173 such as an MRI or DTI scanner, across one of the networks 120, 122, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

Some techniques described in this specification use input variables 154, e.g., data sets characterizing the brain of a patient, which are stored in the memory 134 in corresponding memory locations 155, 156, 157. The techniques can produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle can include i) a fetch operation, which fetches or reads an instruction 131 from a memory location 128, 129, 130; ii) a decode operation in which the control unit 139 determines which instruction has been fetched; and iii) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the techniques described in this specification may be associated with one or more segments of the program 133 and is performed by the register section 144, 145, 146, the ALU 140, and the control unit 139 in the processor 105 working together to perform the fetch, decode, and execute cycles for every instruction in the instruction set for the noted segments of the program 133. Although a cloud-based platform has been described for practicing the techniques described in this specification, other platform configurations can also be used. Furthermore, other hardware/software configurations and distributions can also be used for practicing the techniques described in this specification.

Figure 2:
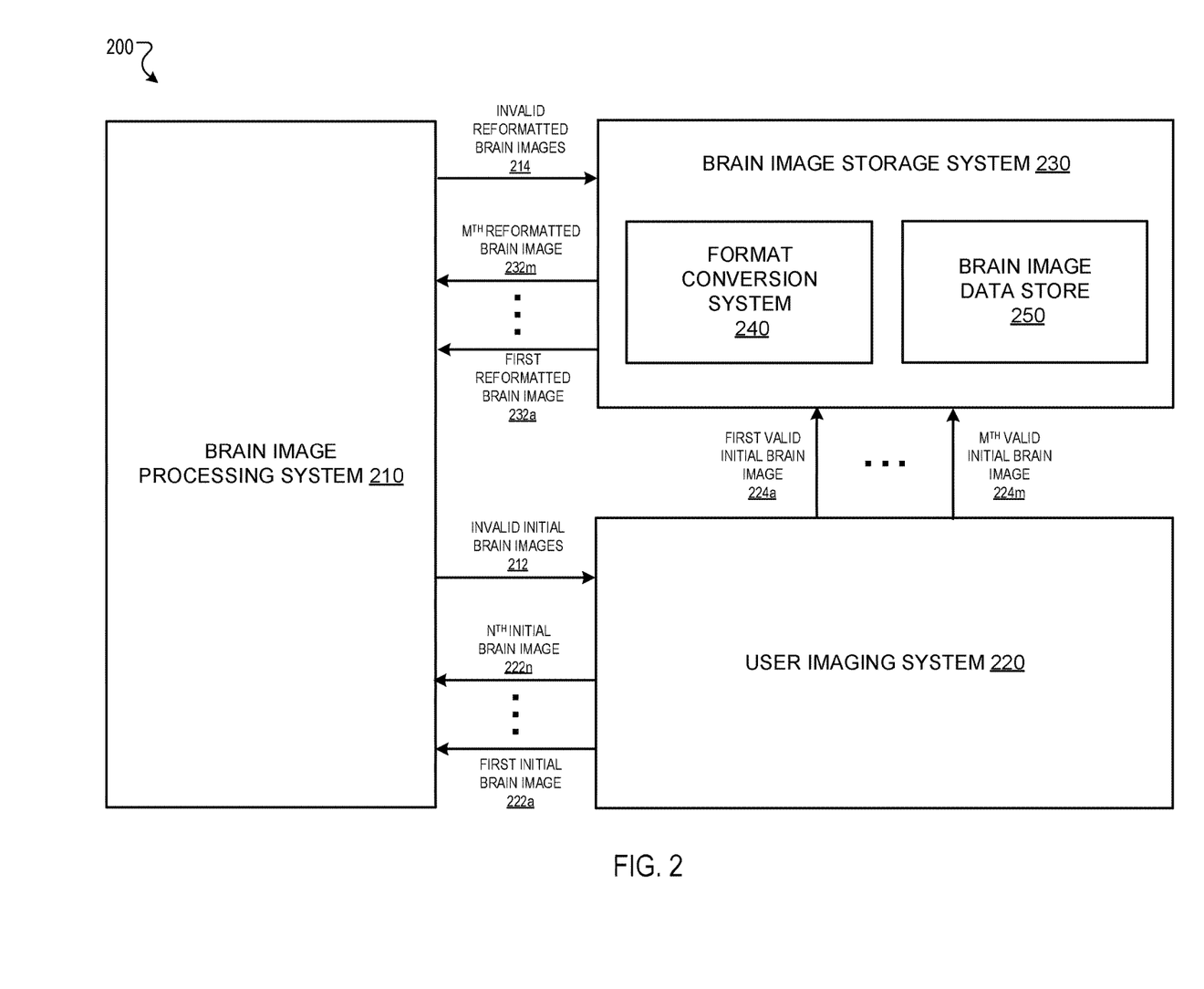
FIG. 2 is a diagram of an example system including a brain image processing system.

FIG. 2 is a diagram of an example system 200. The system 200 is an example of a system implemented as computer programs on one or more computers in one or more locations, in which the systems, components, and techniques described below can be implemented.

The system 200 includes a brain image processing system 210, a user imaging system 220, and a brain image storage system 230.

In some implementations, the user imaging system 220 and the brain image storage system 230 are both local to the user, e.g., components of the same user device. In some other implementations, the user imaging system 220 and the brain image storage system 230 are both non-local to the user, e.g., both hosted within a data center, which can be a distributed computing system having a large number of computers in one or more locations, e.g., hundreds, thousands, or hundreds of thousands of computers in one or more locations. In implementations in which the user imaging system 220 and the brain image storage system 230 are in the same location, the brain image processing system 210 can also be in the same location.

In some other implementations, the user imaging system 220 is local to the user, e.g., a component of a user device, and the brain image storage system 230 is non-local to the user, e.g., hosted on the cloud. In some of these implementations, the brain image processing system 210 can include two components: a first component that is local to the user and that is communicatively connected to the user imaging system 220, and a second component that is on the cloud and that is communicatively connected to the brain image storage system 230. For convenience, the following description will refer to the brain image processing system 210 as a single entity, but it is to be understood that the brain image processing system 210 can have multiple components in multiple different locations.

The user imaging system 220 can obtain one or more brain images characterizing the brain of a patient. For example, the one or more brain images can include one or more MRI images, one or more fMRI images, and/or one or more diffusion tractography images. In some implementations, the user imaging system 220 obtains the brain images from one or more devices that captured the brain images, e.g., the brain imaging device 173 depicted in FIG. 1A. In some other implementations, the user imaging system 220 obtains the brain images from a pre-processing system that has pre-processed the brain images.

In particular, the user imaging system 220 obtains N initial brain images 222*a-n*, where N≥1. The initial brain images 222*a-n* have a first image format, e.g., the DICOM format. Digital Imaging and Communications in Medicine (DICOM) is the international standard for the communication and management of medical imaging information. The user imaging system 220 provides the N initial brain images 222*a-n* to the brain image processing system 210, which is configured to process the initial images to determine whether the initial images are valid.

For example, the brain image processing system 210 can process the initial images according to one or more first tests that correspond to the first image format. Each first test corresponds to one or more validity criteria of the initial brain images 222*a-n*.

In some implementations, the outcome of each first test is a binary validity determination, i.e., either a "Pass" outcome that indicates that the initial brain image meets the corresponding criteria or a "Fail" outcome that indicates that the initial brain image does not meet the corresponding criteria.

In some implementations, one or more of the first tests can have a range of ordinal outcomes, e.g., a value between 0 and 1. The ordinal outcome of a particular first test can be compared against one or more validity criteria corresponding to the particular first test. For example, the brain image may be determined to be invalid if the ordinal outcome satisfies a predetermined threshold. If the brain image satisfies the validity criteria corresponding to each first test, then the brain image can be determined to be valid.

In some implementations, multiple first tests must each fail to satisfy a validity criteria for the brain image to be considered invalid. As a particular example, there may be two tests that each correspond to the same validity criteria, where if the outcome of both tests satisfies a respective predetermined threshold, then the brain image is determined to fail to meet the validity criteria, and otherwise the brain image is determined to meet the validity criteria.

In some implementation, one or more of the first tests can have multiple different nominal outcomes, e.g., "Pass," "Fail," and "No Conclusion." As a particular example, if the outcome of a first test corresponding to a particular validity criteria is "No Conclusion," then the brain image processing system 210 might process the brain image using a different test that also corresponds to the particular validity criteria, e.g., a test that has a binary outcome.

In some implementations, the brain image processing system 210 processes each initial image using a predetermined sequence of first tests. The brain image processing system 210 can then determine the validity of the initial image using the outcomes of the predetermined sequence. As a particular example, each first test in the predetermined sequence might have a binary outcome, so that the initial image is determined to be valid if and only if the outcome of each first test in the predetermined sequence was a "Pass" outcome.

In some other implementations, for each initial image, each first test in a sequence of first tests by which the brain image processing system 210 processes the initial image depends on the outcome of the previous first tests in the sequence. That is, subsequent first tests in the sequence of first tests are themselves determined by the outcome of previous first tests in the sequence. For example, the brain image processing system 210 can maintain a data model that defines, for every possible sequence of first tests and outcomes, either a next first test or a final determination of validity. As a particular example, the system can maintain a tree structure, where each non-leaf node of the tree corresponds to a first test, each branch of the tree corresponds to a particular outcome of the parent node's first test, and each leaf node corresponds to a particular final validity determination of the brain image. When the brain image processing system 210 processes a brain image using a first test and generates an outcome, the system 210 can descend down the tree structure from the node corresponding to the first test, along the branch corresponding to the outcome, and to a second node corresponding to another first test. The system 210 can continue traversing the tree until reaching a leaf node, at which time the system 210 can determine whether the brain image is valid. The system 210 can use any appropriate data model to define how the system 210 should proceed given a particular sequence of first tests and outcomes.

Some example tests are discussed below in reference to Table 1.

After determining, for each initial image, whether the initial image is valid or invalid, the brain image processing system 210 can provide a response back to the user imaging system 220 that includes an identification 212 of the initial brain images that were determined to be invalid. The response can also include, for each invalid initial brain image, an identification of one or more reasons why the initial brain image is invalid, e.g., an error code.

The brain image processing system 210 can also determine whether there are sufficient DICOM instances in a given DICOM series or whether a DICOM series may be missing instances due to file transfer errors. Validity decisions can be made on groups of DICOM instances, series, and/or studies. A single DICOM file is called an instance. Multiple DICOM files that all belong to the same MRI scan (for example, 212 DICOM images that belong to a T1 Anatomical MRI scan) are called a series. Multiple series of DICOM images are called studies. As a particular example, during a first phase of validation, the system 210 can make validity decisions on individual DICOM files. During a second phase of validation, the system 210 can determine whether the collection of DICOM instances in a given series is sufficient, e.g., whether the number of DICOM instances satisfies a threshold. For example, if 50 out of the 212 DICOM images in the T1 Anatomical MRI scan had been discarded (e.g., lost, failed to transfer, or determined to be invalid), then during the second phase the system 210 can determine that the series is insufficient.

The user imaging system 220 can generate data representing a graphical interface that displays to the user i) the identifications of the invalid initial brain images and, optionally, ii) the reasons why each invalid initial brain image is invalid. After the graphical interface data is generated, the graphical interface can be presented to the user on a display device, e.g., on the display device 114 depicted in FIG. 1A.

The graphical interface can include one or more suggestions for actions that the user can take to update the invalid initial images in order to make them valid brain images. As described above, in some implementations the user imaging system 220 is in the same location as the display device, e.g., the computer server module and the display device can each be components of the same device. In some other implementations, the user imaging system 220 is remote, e.g., on the cloud.

In some implementations, the user imaging system 220 can automatically process invalid initial brain images that have failed one or more particular criteria in order to generate updated initial brain images that meet the particular criteria. That is, the user imaging system 220 can determine, according to the identification 212 of the invalid initial brain images and the reasons for invalidity, that one or more of the particular initial brain images failed to meet the particular criteria, and can automatically determine to process the particular initial brain images to generate updated initial brain images that satisfy the particular criteria.

In some implementations, the user imaging system 220 can prompt the user to provide updated initial brain images corresponding to the invalid initial brain images 212.

Upon receiving updated initial brain images, e.g., initial brain images that have either been updated by the user or updated by the user imaging system 220 according to an automatic process, the user imaging system 220 can send the updated initial brain images to the brain image processing system 210, in order to determine that the updated initial brain images are valid. In some other implementations, the user imaging system 220 can automatically determine that the updated initial brain images are valid.

The user imaging system 220 can provide M valid initial brain images 224a-m to the brain image storage system 230, where M≥1. In some cases, M=N, i.e., the user imaging system 220 provides valid versions of each initial image 222a-n to the brain image storage system 230, e.g., if the user imaging system 220 receives updated, valid versions of each initial brain image 222a-n that the brain image processing system 210 determined to be invalid. In some other cases, M<N, i.e., the user imaging system 220 only provides the initial brain images 222a-n that the brain image processing system 210 determined to be valid, before receiving updated versions of the invalid initial brain images.

The brain image storage system 230 includes a brain image data store 250 that is configured to store the brain images of the patient. One or more users, e.g., clinicians that are treating the patient, can access the brain images of the patient stored on the brain image storage system 230. For example, a user can send a request to the brain image data store 250 to retrieve the brain images of the patient and display the brain images on a display device of the user. As another example, a user can request for the brain images of the patient stored in the brain image data store 250 to be processed by one or more machine learning models in order to generate a model output that is clinically relevant to the patient.

The brain image storage system 230 also includes a format conversion system 240 that is configured to process the valid initial brain images 224a-m and generate respective reformatted brain images 232a-m that are in a second format that is different than the first format. For example, the second format can be the NIfTI format. The Neuroimaging Informatics Technology Initiative (NIfTI) is an open file format commonly used to store brain imaging data, e.g., data obtained using Magnetic Resonance Imaging methods. Conversion from the DICOM images format to the NIfTI format is common in the brain imaging domain, as clinical images are typically stored and transferred in the DICOM format, while the NIfTI format has been widely adopted by users in the neuroimaging community. NIfTI models the brain images as a three-dimensional object, whereas DICOM models the brain images as a sequence of two-dimensional image slices; therefore, files having the NIfTI format can be more efficiently handled by some applications, as it stores brain images across a single file instead of dozens or hundreds. Thus, NIfTI can be preferable in some cases, e.g., for some machine learning applications.

In some implementations, the format conversion system 240 is a component of the user imaging system 220 instead of the brain image storage system 230. For example, if the user imaging system 220 is local to the user and the brain image storage system 230 is located on the cloud, then the format conversion system 240 can reformat the brain images locally to the user, and then the user imaging system 220 can provide the reformatted brain images 232*a-m* to the brain image storage system instead of or in addition to the initial brain images 224*a-m*.

After generating the M reformatted brain images 232*a-m*, the brain image storage system 230 can provide the reformatted brain images 232*a-m* to the brain image processing system 210 to determine whether one or more of the brain images 232*a-m* are invalid. For example, the process of reformatting the brain images might have introduced one or more errors to the brain images. As another example, one or more particular validity criteria might only apply to brain images that are in the second format, so the brain image processing system 210 did not test the initial brain images 222*a-n*, which were in the first format, for the particular validity criteria.

In particular, the brain image processing system 210 can process the reformatted images 232*a-m* according to one or more second tests that correspond to the second image format. Each second test corresponds to one or more validity criteria of the reformatted brain images.

As described above, in some implementations, the outcome of each second test is a binary validity determination. In some other implementations, one or more of the second tests can have a range of ordinal outcomes, e.g., a value between 0 and 1. In some other implementations, one or more of the second tests can have multiple different nominal outcomes, e.g., "Pass," "Fail," and "No Conclusion."

As described above, in some implementations, the brain image processing system 210 processes each reformatted image using a predetermined sequence of second tests. The brain image processing system 210 can then determine the validity of the reformatted image using the outcomes of the predetermined sequence. In some other implementations, for each reformatted image, each second test in a sequence of second tests by which the brain image processing system 210 processes the reformatted image depends on the outcome of the previous second tests in the sequence. For example, the brain image processing system 210 can maintain a data model that defines, for every possible sequence of second tests and outcomes, either a next second test or a final determination of validity.

Some example tests are discussed below in reference to Table 1.

After determining, for each reformatted image, whether the reformatted image is valid or invalid, the brain image processing system 210 can provide a response back to brain image storage system 230 that includes an identification 214 of the reformatted brain images that were determined to be invalid. The response can also include, for each invalid reformatted brain image, an identification of one or more reasons why the reformatted brain image is invalid, e.g., an error code.

The brain image storage system 230 can generate data representing a graphical interface that displays to the user i) the identifications of the invalid reformatted brain images and, optionally, ii) the reasons why each invalid reformatted brain image is invalid. After the graphical interface data is generated, the graphical interface can be presented to the user on a display device, e.g., on the display device 114 depicted in FIG. 1A. The graphical interface can include one or more suggestions for actions that the user can take to update the invalid reformatted images in order to make them valid brain images.

In some implementations, the brain image storage system 230 can automatically process invalid reformatted brain images that have failed one or more particular criteria in order to generate updated reformatted brain images that meet the particular criteria. That is, the brain image storage system 230 can determine, according to the identification 214 of the invalid reformatted brain images and the reasons for invalidity, that one or more of the particular reformatted brain images failed to meet the particular criteria, and can automatically determine to process the particular reformatted brain images to generate updated reformatted brain images that satisfy the particular criteria.

In some implementations, the brain image storage system 230 can prompt the user to provide updated reformatted brain images corresponding to the invalid reformatted brain images 214.

Upon receiving updated reformatted brain images, e.g., reformatted brain images that have either been updated by the user or updated according to an automatic process, the brain image storage system 230 can send the updated reformatted brain images to the brain image processing system 210, in order to determine that the updated reformatted brain images are valid. In some other implementations, the brain image storage system 230 can automatically determine that the updated reformatted brain images are valid.

Each valid reformatted brain image 232*a-m* is stored in the brain image data store 250. In some implementations, the brain image data store 250 stores each valid brain image in both the first format and the second format. In some other implementations, the brain image data store 250 stores each valid brain image only in the second format.

The brain images stored by the brain image data store 250 can be used by clinicians to provide treatment to the patient. For example, the clinicians can submit requests for the brain images to be displayed or further processed to determine whether the patient has a brain disease or determine a recommended treatment for the patient.

TABLE 1

| Code | Error Message | Description | Example Recommendation |
|------|---------------|-------------|------------------------|
| 1001 | Error in accessing NIfTI contents | The header or the data from the NIfTI file cannot be accessed | View the image using an external viewer |
| 1002 | The shape of data is not consistent | The shape of the diffusion-weighted imaging (DWI) data sequence, the bval file and/or the bvec file is not consistent. The bval and bvec files include metadata containing | Check that the (x, y, z, t) coordinates of the DWI sequence has the same shape |

TABLE 1-continued

| Code | Error Message | Description | Example Recommendation |
|---|---|---|---|
| 1003 | DWI sequence does not have sufficient gradient directions for CSD | the gradient directions and diffusion weighting For a DWI sequence to be usable for constrained spherical deconvolution (CSD), it needs to have a certain threshold of gradient directions | as the bval/bvec files Check that the DWI sequence has at least, e.g., 24 directions in the bval file and the bvec file |
| 1004 | fMRI sequence does not have sufficient time frames | For an fMRI sequence to be usable for connectomic analysis, it needs to have a certain threshold of time frames | Chech that the fMRI sequence has at least, e.g., 60 time frames |
| 1005 | Image data is 0 in the NIfTI image | The voxel data in the generated NIfTI file does not appear to have any valid values | Check the integrity of the uploaded data |
| 1006 | Image data is not consistent with neuroimaging data | The generated NIfTI image does not appear consistent with standard neuroimaging data | Check the integrity of the uploaded data |
| 1007 | Image does not have correct 3D dimensionality | Anatomical files should generally be three-dimensional. The uploaded data does not have three dimensions | Check the dimensionality of the uploaded data |
| 1008 | Image does not have correct 4D dimensionality | Echo Planar Imaging (EPI) files should generally be four-dimensional sequences. The uploaded data does not have four dimensions | Check the dimensionality of the uploaded data |
| 1009 | Errors performing tractography | There were errors performing CSD. | Ensure that the uploaded DWI sequence has a roughly uniform distribution of gradient directions |
| 2001 | Error in loading DICOM image | The uploaded DICOM file cannot be opened using the standard tooling without error | Check the integrity of the uploaded DICOM file |
| 2002 | Invalid DICOM metadata | One of the following metadata tags in the uploaded DICOM file is invalid: (0002,0001) File Meta Information Version (0002,0012) Implementation Class UID (0002,0013) Implementation Version Name (0002,0002) Media Storage SOP Class UID (0002,0003) Media Storage SOP Instance UID (0002,0010) Transfer Syntax UID | Check the metadata tags in the uploaded DICOM file |
| 2003 | Invalid DICOM file schema | The uploaded DICOM file does not match the standard schema for MR images | Check schema of the uploaded DICOM file |

Table 1 is a table of a few example validity criteria for determining that a brain image of a patient is invalid. Each example criteria includes an example error code and error message that might be presented to the user if the criteria has not been met for a particular image, as well as a description of the criteria and an example recommendation for updating the image that might be presented to the user. The error codes and messages are exemplary only; in general, error codes can be any string of alphanumeric characters, and error messages can be any text that describes the error. In some implementations, an error code is not presented to the user, and only the error message or some other notification is displayed to the user to alert the user of the particular error. Generally, each criteria corresponding to an error code that begins with '1' relates to a NIfTI image, while each criteria corresponding to an error code that begins with '2' relates to a DICOM image.

Figure 3:
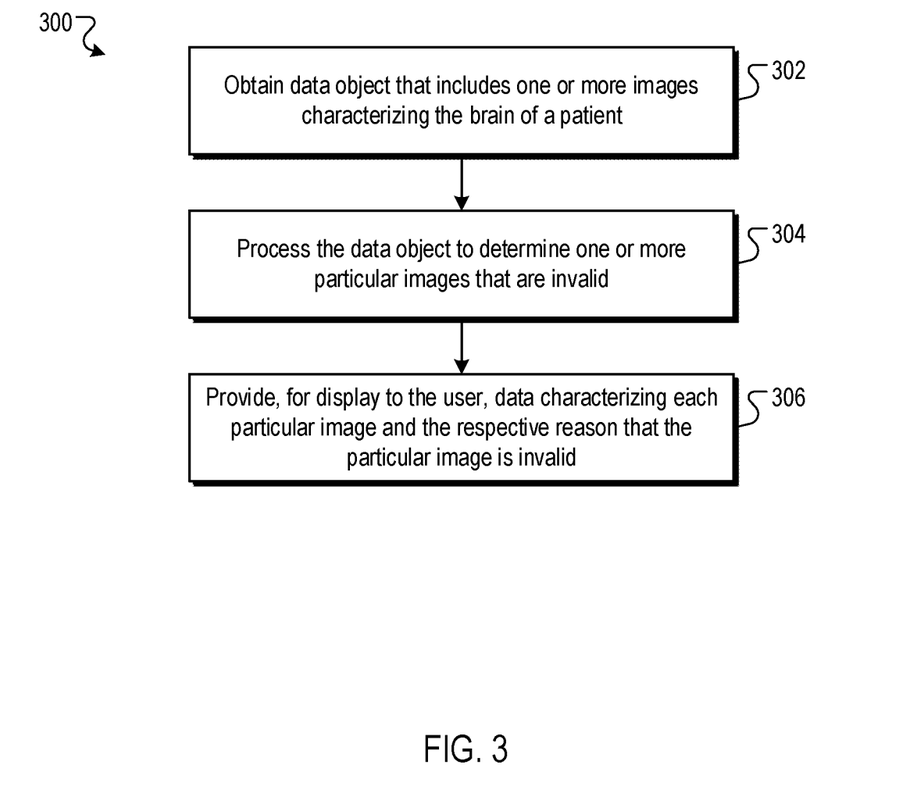
FIG. 3 is a flowchart of an example process for determining that one or more brain images are invalid.

FIG. 3 is a flowchart of an example process 300 for determining that one or more brain images are invalid. The process 300 can be implemented by one or more computer programs installed on one or more computers and programmed in accordance with this specification. For example, the process 300 can be performed by the computer server module depicted in FIG. 1A. For convenience, the process 300 will be described as being performed by a system of one or more computers.

The system obtains a data object that includes one or more images characterizing the brain of a patient (step 302). The images can include one or more of: one or more MRI images, one or more fMRI images, or one or more diffusion tractography images.

For example, the system can obtain the data object by obtaining, using a local system of a user device of the user, the data object, and then uploading the data object from the local system of the user device to a non-local system of a non-local device, e.g, a system hosted on the cloud.

The system processes the data object to determine one or more particular images that are invalid (step 304). The system can process the data system using a local system of a user device of the user, a non-local system of a non-local device, or both.

The system provides, for display to the user on a graphical interface, data characterizing, for each particular image, the particular image and one or more reasons that the particular image is invalid (step 306). The one or more reasons can be selected from a set of possible reasons that an image may be invalid, e.g., a set that includes one or more of the criteria listed in Table 1.

In response to determining that one or more of the images are valid, the system can store the valid images in a location that is accessible by a client device. For example, in response to a request from the client device, the system can process the one or more valid images using an image processing system to generate a clinically relevant output for the user, e.g., an image processing machine learning model.

As a particular example, the clinically relevant output can include connectivity data that characterizes, for each pair of parcellations of multiple parcellations, a correlation between brain activity of the first parcellation and brain activity of the second parcellation in the brain of the patient. For example, the clinically relevant output can include a correlation matrix characterizing the correlation between the brain activity of the multiple parcellations.

Figure 4:
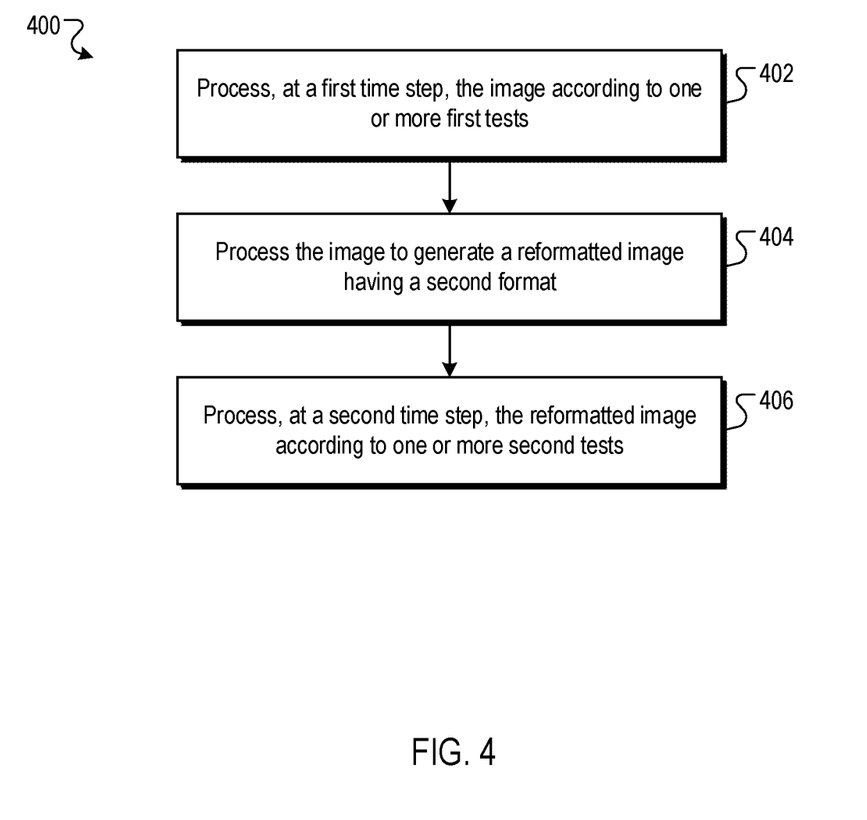
FIG. 4 is a flowchart of an example process for processing a brain image in order to determine whether the brain image is invalid.

FIG. 4 is a flowchart of an example process 400 for processing a brain image in order to determine whether the brain image is invalid. The process 400 can be implemented by one or more computer programs installed on one or more computers and programmed in accordance with this specification. For example, the process 400 can be performed by the computer server module depicted in FIG. 1A. For convenience, the process 400 will be described as being performed by a system of one or more computers.

The system processes, at a first time step, the image according to one or more first test (step 402). The image has a first format, and the one or more first tests can each correspond to the first format.

As a particular example, the system can process, for each of multiple predetermined first tests, the image according to the first test to generate a respective test output, and then determine whether the image is valid according to the multiple generated test outputs.

The system processes the image to generate a reformatted image having a second format (step 404). The second format is different than the first format.

The system processes, at a second time step, the reformatted image according to one or more second tests (step 406).

As a particular example, the system can process, for each of multiple predetermined second tests, the image according to the second test to generate a respective test output, and then determine whether the image is valid according to the multiple generated test outputs.

In some implementations, the system processes each image at the first time step using a local system of a user device of the user, and processes each reformatted image at the second time step using a non-local system of a non-local device.

In evaluating individual DICOMs, embodiments described in this specification can receive more than 1,000, more than 10,000, or more than 100,000 individual DICOM images for assessment within a short period of time, e.g., in less than an hour, less than 30 minutes, less than 10 minutes, less than 5 minutes, or less than a minute. Given that the images can be of human patients, time is of the essence especially if the patient requires urgent, time-sensitive diagnosis and/or treatment.

Furthermore, embodiments described in this specification can be used to evaluate whether there are sufficient DICOM instances to form a DICOM series. The embodiments can need to determine whether a subset of DICOM instances (e.g., more than 900 DICOM instances) belong to a particular DICOM series out of a set of DICOM instances submitted (e.g., out of more than 10,000 DICOM instances submitted). To evaluate whether the series is sufficient, an embodiment of such a system can: identify the more than 900 instances that belong to the same series; extract parameters to identify where in a 4D matrix each of these instances belong; determine whether there is a mismatch in the number of instances, the length of the series, and/or the number of points in 3D space to identify whether data may be missing from the series.

With regard to Nifti images, evaluation of CSD fit enables quick feedback to a user on an item that would otherwise only be realized much later on in the processing pipeline.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g., a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain some cases, multitasking and parallel processing may be advantageous.

What is claimed is:

1. A method comprising:
obtaining a data object comprising one or more images characterizing a brain of a patient;
processing the data object to determine one or more particular images that are invalid, comprising, for each image:
processing, for each of a plurality of predetermined tests, the image according to the test to generate a respective test output; and
determining whether the image is invalid according to the plurality of generated test outputs; and
providing, for display to a user on a graphical interface, data characterizing i) each particular image and ii) a respective reason that each particular image is invalid selected from a set of possible reasons that an image may be invalid.

2. The method of claim 1, wherein the set of possible reasons that an image may be invalid comprises one or more of:
a header or data from a file of the image cannot be accessed;
a shape of data characterizing the image is inconsistent;
the image does not have enough time frames or enough gradient directions;
data characterizing the image is not consistent with standard neuroimaging data;
the image does not have correct 3D or 4D dimensionality;
metadata of the image is invalid;
a file of the image does not match a standard schema;
a file of the image cannot be opened using standard tooling;
voxel data characterizing the image does not have valid values; or
voxel data characterizing the diffusion weighted image is not sufficient for constrained spherical deconvolution (CSD).

3. The method of claim 2, wherein the images characterizing the brain of the patient comprise one or more of:
one or more MRI images;
one or more fMRI images; or
one or more diffusion tractography images.

4. The method of claim 3, wherein determining that an image is invalid comprises one or more of:
determining that the image has been corrupted;
determining that the image is improperly formatted; or
determining that the image does not follow one or more predetermined protocols.

5. The method of claim 4, wherein obtaining the data object comprises:
obtaining, by a local system of a user device of the user, the data object; and
uploading the data object from the local system of the user device to a non-local system of a non-local device.

6. The method of claim 5, wherein processing the data object comprises one or more of:
processing the data object using a local system of a user device of the user; or
processing the data object using a non-local system of a non-local device.

7. The method of claim 6, wherein:
each image in the data object has a first format; and
processing the data object to determine one or more particular images that are invalid comprises:
processing, at a first time step, each image according to one or more first tests;
processing, for each image, the image to generate a reformatted image having a second format; and
processing, at a second time step, each reformatted image according to one or more second tests.

8. The method of claim 7, wherein the first format is a DICOM format and the second format is a NIfTI format.

9. The method of claim 8, wherein:
processing each image at the first time step comprises processing each image using a local system of a user device of the user; and
processing each reformatted image at the second time step comprises processing each reformatted image using a non-local system of a non-local device.

10. The method of claim 9, further comprising, in response to determining that one or more images are valid, processing the one or more valid images using an image processing system to generate a clinically relevant output.

11. The method of claim 10, wherein the clinically relevant output comprises connectivity data that characterizes, for each first parcellation and second parcellation of a plurality of parcellations, a correlation between brain activity of the first parcellation and brain activity of the second parcellation in the brain of the patient.

12. The method of claim 11, further comprising:
generating, for each of one or more of the particular images, a recommendation for updating the particular image to make the particular image valid; and
providing, for display to the user on the graphical interface, data characterizing the one or more recommendations.

13. The method of claim 1, wherein:
each of the plurality of predetermined tests corresponds to one or more respective validity criteria,
for each image, the respective test output for each predetermined test is indicative of whether the image satisfies the corresponding validity criteria, and
providing data characterizing a respective reason that each particular image is invalid comprises providing data characterizing, for each particular image, the validity criteria that are not satisfied by the particular image according to the respective test outputs of the corresponding predetermined tests.

14. A system comprising one or more computers and one or more storage devices storing instructions that are operable, when executed by the one or more computers, to cause the one or more computers to perform operations comprising:
obtaining a data object comprising one or more images characterizing a brain of a patient;
processing the data object to determine one or more particular images that are invalid, comprising, for each image:
processing, for each of a plurality of predetermined tests, the image according to the test to generate a respective test output; and
determining whether the image is invalid according to the plurality of generated test outputs; and
providing, for display to a user on a graphical interface, data characterizing i) each particular image and ii) a respective reason that each particular image is invalid selected from a set of possible reasons that an image may be invalid.

15. The system of claim 14, wherein the set of possible reasons that an image may be invalid comprises one or more of:
a header or data from a file of the image cannot be accessed;

a shape of data characterizing the image is inconsistent;
the image does not have enough time frames or enough gradient directions;
data characterizing the image is not consistent with standard neuroimaging data;
the image does not have correct 3D or 4D dimensionality;
metadata of the image is invalid;
a file of the image does not match a standard schema;
a file of the image cannot be opened using standard tooling;
voxel data characterizing the image does not have valid values; or
voxel data characterizing the diffusion weighted image is not sufficient for constrained spherical deconvolution (CSD.

16. The system of claim 15, wherein the images characterizing the brain of the patient comprise one or more of:
one or more MRI images;
one or more fMRI images; or
one or more diffusion tractography images.

17. The system of claim 16, wherein determining that an image is invalid comprises one or more of:
determining that the image has been corrupted;
determining that the image is improperly formatted; or
determining that the image does not follow one or more predetermined protocols.

18. The system of claim 17, wherein obtaining the data object comprises:
obtaining, by a local system of a user device of the user, the data object; and
uploading the data object from the local system of the user device to a non-local system of a non-local device.

19. The system of claim 18, wherein processing the data object comprises one or more of:
processing the data object using a local system of a user device of the user; or
processing the data object using a non-local system of a non-local device.

20. The system of claim 14, wherein:
each of the plurality of predetermined tests corresponds to one or more respective validity criteria,
for each image, the respective test output for each predetermined test is indicative of whether the image satisfies the corresponding validity criteria, and
providing data characterizing a respective reason that each particular image is invalid comprises providing data characterizing, for each particular image, the validity criteria that are not satisfied by the particular image according to the respective test outputs of the corresponding predetermined tests.

21. One or more non-transitory storage media storing instructions that when executed by one or more computers cause the one or more computers to perform operations comprising:
obtaining a data object comprising one or more images characterizing a brain of a patient;
processing the data object to determine one or more particular images that are invalid, comprising, for each image:
processing, for each of a plurality of predetermined tests, the image according to the test to generate a respective test output; and
determining whether the image is invalid according to the plurality of generated test outputs; and
providing, for display to a user on a graphical interface, data characterizing i) each particular image and ii) a respective reason that each particular image is invalid selected from a set of possible reasons that an image may be invalid.

* * * * *